United States Patent [19]
Diem et al.
[11] 3,966,727
[45] June 29, 1976

[54] MANUFACTURE OF PHTHALO-BIS-GUANAMINES

[75] Inventors: Hans Diem; Christian Dudeck; Gunter Lehmenn, all of Ludwigshafen, Germany

[73] Assignee: BASF Aktiengesellschaft, Ludwigshafen (Rhine), Germany

[22] Filed: Dec. 16, 1974

[21] Appl. No.: 533,145

[30] Foreign Application Priority Data

Dec. 29, 1973 Germany ........................... 2365180

[52] U.S. Cl. ........................................... 260/249.9
[51] Int. Cl.$^2$ ........................................ C07D 251/48
[58] Field of Search ................................ 260/249.9

[56] References Cited

UNITED STATES PATENTS 3,269,944 8/1966 Hedenburg et al. ......... 260/249.9 X

*Primary Examiner*—John M. Ford
*Attorney, Agent, or Firm*—Johnston, Keil, Thompson & Shortleff

[57] ABSTRACT

Manufacture of phthalo-bis-guanamines by reaction of phthalodinitriles with dicyandiamide in the presence of basic compounds and dialkylsulfoxides. The products are starting materials for the manufacture of synthetic resins, plastics, textile auxiliaries, plant protection agents and dyes.

10 Claims, No Drawings

MANUFACTURE OF PHTHALO-BIS-GUANAMINES

The invention relates to a process for the manufacture of phthalo-bis-guanamines by reaction of phthalodinitriles with dicyandiamide in the presence of basic compounds and dialkylsulfoxides.

It is known from Annalen, 376, 181 (1910) that phenylguanamine (1-phenyl-3,5-diaminotriazine) can be manufactured by reaction of benzoyl chloride and diguanide sulfate in the presence of sodium hydroxide solution. The starting material for the process, diguanide, is difficult and uneconomical to prepare and is unsuitable for use particularly on an industrial scale, as the process would lack simplicity, economy and reliability.

A different process for the reaction of nitriles with dicyandiamide in the presence of alkali has therefore been preferred (U.S. Pat. No. 2,684,366). Primary or secondary alcohols are used as the solvents. However, the manufacture of isophthalo-bis-guanamine was not described, nor was isophthalodinitrile mentioned as a starting material. The process in question gives unsatisfactory yields of impure phthalo-bis-guanamine and terephthalo-bis-guanamine and particularly poor results in the case of isophthalo-bis-guanamine if the instructions of the above U.S. patent are applied to the manufacture of the isophthalo compound. Essentially, only one nitrile group of isophthalodinitrile reacts in this process.

German Pat. No. 1,019,310 teaches an analogous reaction in the absence of organic solvents but in the presence of ammonia and alkaline compounds at temperatures above 130°C under pressure. Liquid ammonia is the preferred solvent. This patent discloses that in processes carried out in the presence of organic solvents, for example glycols, a large excess of dicyandiamide must be used to prevent decomposition of the reaction mixture, with elimination of ammonia. Phthalodinitrile and isophthalodinitrile are not mentioned as starting materials, nor is the manufacture of the corresponding bis-guanamines disclosed. If the instructions of the above German Patent are applied to the manufacture of these guanamines, side-reactions of the dicyandiamide take place at the elevated temperatures used, i.e. the dicyandiamide decomposes on heating to form melamine and ammonia (Beilstein, Handbuch der organischen Chemie (Springer, Berlin 1921), 4th edition, vol. III, page 91). In addition, the working up required is laborious since the reaction mixture is obtained in the form of a hard solid which is difficult to detach from the walls of the vessel and difficult to comminute. The process is therefore unsatisfactory, particularly on an industrial scale, as it lacks simplicity and reliability and purification operations cannot be avoided.

Japanese Published Application 27,631/1968 discloses a process for the reaction of isophthalodinitrile with dicyandiamide at atmospheric pressure and temperatures from 100° to 120°C in the presence of potassium hydroxide; the only solvent specified is methylcellosolve. Large amounts of this comparatively expensive solvent have to be used during the reaction and during working up of the end product, and can only be recovered with difficulty. The process is unsatisfactory in that it does not provide a simple method, a short reaction time, easy and economical isolation of the end product from the reaction mixture and high yields of pure end product.

The present invention relates to a new process for the simpler and more economical manufacture of phthalo-bis-guanamines in better yield and purity.

We have found that an advantageous method of obtaining phthalo-bis-guanamines of the formula

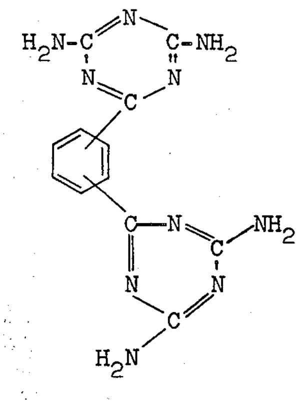

I wherein the two substituents on the phenylene ring are in the o-, m- or p-position to one another, is the reaction of phthalodinitriles of the formula

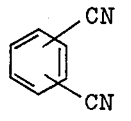

II wherein the two substituents are in the o-, m- or p-position to one another, with dicyandiamide in the presence of inorganic, basic compounds and organic solvents, wherein the solvents are aliphatic sulfoxides, sulfones or formamides of the formula

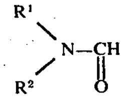

III in which $R^1$ and $R^2$ can be identical or different and each is hydrogen or an aliphatic or aromatic radical or $R^1$ and $R^2$ together with the adjacent nitrogen are members of a heterocyclic ring.

Where isophthalodinitrile is used, the reaction can be represented by the following equation:

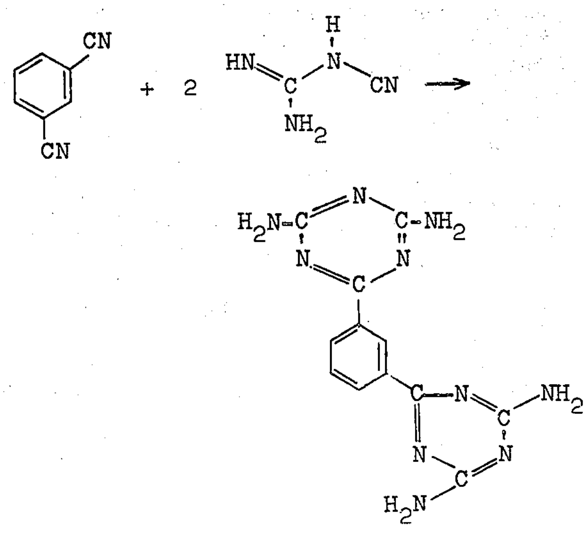

Compared to conventional processes, the process according to the invention gives phthalo-bis-guanamines more simply and more economically, and in better yield and better purity. The process can with advantage be carried out at lower temperatures, under atmospheric pressure, and using a short reaction time. Involved or costly working up is avoided. No significant formation of byproducts resulting from the reaction of only one nitrile group is observed. All these advantages of the process, especially when manufacturing isophthalo-bis-guanamine, are surprising in the light of the state of the art.

Amongst the three starting materials phthalodinitrile, terephthalodinitrile and isophthalodinitrile, terephthalodinitrile and especially isophthalodinitrile are preferred, and correspondingly the preferred end products are terephthalo-bis-guanamine and especially isophthalo-bis-guanamine. The starting materials can be reacted in stoichiometric amounts or with an excess of dicyandiamide, preferably using a ratio of from 2 to 3 moles of dicyandiamide per mole of starting material II.

The reaction is advantageously carried out at from 20° to 120°C, desirably from 50° to 120°C and preferably from 50° to 95°C, under super-atmospheric or sub-atmospheric pressure or, advantageously, at atmospheric pressure, and continuously or batchwise. The aliphatic sulfoxides or sulfones used are generally those of the formula

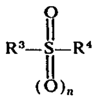

IV, wherein $R^3$ and $R^4$ can be identical or different and each is an aliphatic radical, preferably alkyl or alkenyl, or $R^3$ and $R^4$ together are an aliphatic radical, preferably alkylene, which forms a ring with the adjacent sulfur, and *n* is 0 or 1. Particularly advantageously, alkyl is of 1 to 8, especially of 1 to 4, carbon atoms, alkenyl is of 2 to 8, preferably 2 to 4, carbon atoms and alkylene is of 2, 3 and especially 4 and 5 carbon atoms. The above radicals may be substituted by groups inert under the reaction conditions, for example carboxylic acid amide, or alkoxy of 1 to 3 carbon atoms.

Preferred materials III are those in which $R^1$ and $R^2$ can be identical or different and each is hydrogen, an alkyl of 1 to 8, especially of 1 to 4, carbon atoms or phenyl, or $R^1$ and $R^2$ together with the adjacent nitrogen are members of a saturated heterocyclic 5- or 6-ring which can contain a further nitrogen or an oxygen atom. The said radicals and rings can also be substituted by groups and/or atoms inert under the reaction conditions, for example alkyl or alkoxy each of 1 to 4 carbon atoms.

Examples of suitable solvents are dimethyl sulfoxide, diethyl sulfoxide, tetramethylene sulfoxide, pentamethylene sulfoxide, dipropyl sulfoxide, diisopropyl sulfoxide, di-n-butyl sulfoxide, di-sec.-butyl sulfoxide, diisobutyl sulfoxide, diallyl sulfoxide, dodecyl vinyl sulfoxide, diisoamyl sulfoxide, ε-aminopentylmethyl sulfoxide, diamyl sulfoxide, divinyl sulfoxide, tetramethylene sulfone, 3,4-dimethyl-tetramethylene sulfone, 3-methyltetramethylene sulfone, pentamethylene sulfone, divinyl sulfone, diethyl sulfone, 2,2'-dimethoxydiethyl sulfone, di-n-butyl sulfone, ethyl-n-propyl sulfone, di-n-propyl sulfone, formamide, formanilide, N-formylpiperidine, N-formylpyrrolidine, N-formylmorpholine, N,N-diethyl-formamide, N-isobutyl-formamide, N-methyl-formamide, form(p-chloro)-anilide and especially N-methyl-formanilide and N,N-dimethyl-formamide; and mixtures thereof. Dimethyl sulfoxide, tetramethylene sulfone and dimethylformamide are particularly preferred. Advantageously, from 250 to 350% by weight, preferably from 200 to 400% by weight, of organic solvent, based on starting material II, are used. If appropriate, water can also be added, preferably in amounts of from 30 to 500% by weight, based on inorganic compound, e.g. in order to dissolve the inorganic basic compound.

Preferred inorganic basic compounds are alkaline earth metal compounds, zinc compounds and especially alkali metal compounds and mixtures thereof. Advantageous alkali metal compounds, zinc compounds and alkaline earth metal compounds are the hydroxides, oxides, carbonates, bicarbonates, salts of weak or polybasic acids and alcoholates of calcium, barium, zinc, lithium and especially sodium and potassium. Examples of the basic compounds which can be used are potassium hydroxide, sodium hydroxide, potassium carbonate, sodium carbonate, lithium carbonate, sodium bicarbonate, potassium bicarbonate, calcium hydroxide, barium oxide, calcium carbonate, zinc oxide, potassium methylate, sodium acetate, sodium propionate, and sodium ethylene-glycolate, methylate, ethylate and tripropyleneglycolate. The amounts of basic compounds advantageously used per mole of starting material II are from 0.05 to 1 equivalent, preferably from 0.25 to 0.75 equivalent.

The reaction can be carried out as follows: a mixture of the starting materials, the solvent and the basic compound is reacted for from 0.7 to 10 hours, preferably from 1 to 3 hours, at the reaction temperature. The end product is then isolated from the reaction mixture by conventional methods, for example by adding water to the mixture and filtering. In most cases, the product can be used directly in the form in which it is obtained, but if appropriate it can be washed with water and a suitable solvent, for example methanol, and dried.

The end products which can be manufactured by the process of the invention are valuable starting materials for the manufacture of synthetic resins, plastics, textile auxiliaries, plant protection agents and dyes. For example, they can be reacted with formaldehyde and, optionally in an acid medium, with aliphatic alcohols, thus obtaining resins which can be used for moldings and coatings, baking enamels, fiber treatment agents, impregnating resins, paper impregnation and adhesives. Terephthalo-bis-guanamine and especially isophthalo-bis-guanamine are advantageous stabilizers for aqueous formaldehyde solutions, when used by the method disclosed in German Published Application P 23 58 856.9. Regarding details of their use, reference may be made to the said publications.

The parts in the examples which follow are by weight.

EXAMPLE 1

187 Parts of potassium hydroxide are dissolved in 8,670 parts of dimethyl sulfoxide at 50°C in a stirred vessel. 853 parts of isophthalodinitrile and 1,340 parts of dicyandiamide are added to the solution obtained, the mixture is heated to 85°C for 3 hours, 15,000 parts of water are then added and the resulting end product is filtered off, washed with 8,000 parts of water and 8,000 parts of methanol and dried at 100°C. 1,913 parts (97% of theory) of isophthalo-bis-guanamine melting above 400°C are obtained.

EXAMPLE 2

The reaction is carried out analogously to Example 1, but after heating for three hours the reaction mixture is allowed to cool slowly. The end product precipitates in a very pure form (98% by weight) and is filtered off. 1,913 parts (97% of theory) of isophthalo-bis-guanamine melting above 400°C are obtained.

EXAMPLE 3

28 Parts of potassium hydroxide and 2,000 parts of dimethyl sulfoxide are first introduced into a continuously operated stirred kettle equipped with a heat exchanger, and 128 parts per hour of isophthalodinitrile, 170 parts per hour of dicyandiamide, 4 parts per hour of potassium hydroxide and 200 parts per hour of dimethyl sulfoxide are added by means of metering devices. The reaction temperature is 80°C and the average residence time is 3 hours. The reaction mixture leaving the kettle is cooled and the end product is separated from the solvent by means of a centrifuge. The solvent, which still contains some of the initial mixture is recycled to the stirred kettle. 266 parts (90% of theory) of isophthalo-bis-guanamine melting above 400°C are obtained hourly.

EXAMPLE 4

The reaction is carried out analogously to Example 1, but instead of dimethyl sulfoxide 8,670 parts of dimethylformamide and 100 parts of water are used as the solvent. 1,913 parts (97% of theory) of isophthalo-bis-guanamine melting above 435°C are obtained.

EXAMPLE 5

The reaction is carried out analogously to Example 1, but at 120°C and using 853 parts of terephthalodinitrile instead of isophthalodinitrile. 1,676 parts (85% of theory) of terephthalo-bis-guanamine melting at 400°C are obtained.

We claim:

1. A process for the manufacture of a phthalo-bis-guanamine of the formula

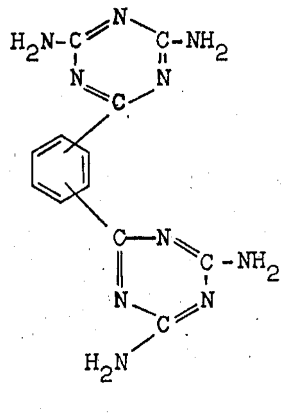

I wherein the two substituents on the phenylene ring are in the o-, m- or p-position to one another, by reaction of phthalodinitriles of the formula

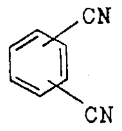

II wherein the two substituents are in the o-, m- or p-position to one another, with dicyandiamide in the presence of an inorganic, basic compound and an organic solvent, wherein the solvent is a sulfoxide or a sulfone of the formula

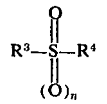

IV, in which $R^3$ and $R^4$ can be identical or different radicals and each is alkyl of 1 to 8 carbon atoms or alkenyl of 2 to 8 carbon atoms, or $R^3$ and $R^4$ together are alkylene of 2 to 5 carbon atoms, or the said radicals substituted by carboxylic acid amide or alkoxy of 1 to 3 carbon atoms, and n is 0 or 1; or said solvent is a formamide of the formula

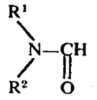

III in which $R^1$ and $R^2$ can be identical or different and each is hydrogen, alkyl of 1–8 carbon atoms, phenyl, or said alkyl or said phenyl substituted by alkyl or alkoxy respectively having 1–4 carbon atoms or $R^1$ and $R^2$ together with the adjacent nitrogen form a 5- or 6-membered heterocyclic ring, optionally containing another nitrogen atom or an oxygen atom and optionally substituted by alkyl or alkoxy respectively having 1–4 carbon atoms.

2. A process as claimed in claim 1, wherein the reaction is carried out using from 2 to 3 moles of dicyandiamide per mole of starting material II.

3. A process as claimed in claim 1, wherein the reaction is carried out at from 20° to 120°C.

4. A process as claimed in claim 1, wherein the reaction is carried out at from 50° to 120°C.

5. A process as claimed in claim 1, wherein the reaction is carried out at from 50° to 95°C.

6. A process as claimed in claim 1, wherein the reaction is carried out with dimethyl sulfoxide, diethyl sulfoxide, tetramethylene sulfoxide, pentamethylene sulfoxide, dipropyl sulfoxide, diisopropyl sulfoxide, di-n-butyl sulfoxide, di-sec-butyl sulfoxide, diisobutyl sulfoxide, diallyl sulfoxide, dodecyl vinyl sulfoxide, diisoamyl sulfoxide, ϵ-aminopentyl methyl sulfoxide, diamyl sulfoxide, divinyl sulfoxide, tetramethylene sulfone, 3,4-dimethyl-tetramethylene sulfone, 3-methyl-tetramethylene sulfone, pentamethylene sulfone, divinyl sulfone, diethyl sulfone, 2,2'-di-methoxy-diethyl sulfone, di-n-butyl sulfone, ethyl n-propyl sulfone, di-n-propyl sulfone, formamide, formanilide, N-formylpiperidine, N-formulpyrrolidine, N-formylmorpholine, N,N-diethyl-formamide, N-isobutyl-formamide, N-methylformamide, form-(p-chloro)-anilide, N-methylformanilide or N,N-dimethyl-formamide.

7. A process as claimed in claim 1, wherein the reaction is carried out with from 250 to 350% by weight of organic solvents, based on the starting material II.

8. A process as claimed in claim 1, wherein the reaction is carried out with from 0.05 to 1 equivalent of basic compound per mole of starting material II.

9. A process as claimed in claim 1 wherein said solvent is a compound of the formula III in which $R^1$ and $R^2$ are identical or different and each is hydrogen, alkyl of 1–8 carbon atoms, phenyl, or said alkyl or said phenyl substituted by alkyl or alkoxy respectively having 1–4 carbon atoms or $R^1$ and $R^2$ together with the adjacent nitrogen represent piperidino, pyrrolidino, or morpholino.

10. A process as claimed in claim 1 wherein said solvent is a member selected from the group consisting of N-methyl-formanilide, N,N-dimethyl-formamide, dimethyl sulfoxide and tetramethylene sulfone.

* * * * *